US011717618B2

(12) United States Patent
Carroll et al.

(10) Patent No.: US 11,717,618 B2
(45) Date of Patent: Aug. 8, 2023

(54) MEDICINAL FLUID DELIVERY DEVICES AND ASSOCIATES METHODS FOR ADVANCING AND RETRACTING NEEDLES

(71) Applicant: Duke University, Durham, NC (US)

(72) Inventors: Kathleen Carroll, Durham, NC (US); Ru-Rong Ji, Durham, NC (US); Linda Gray-Leithe, Durham, NC (US); Timothy Amrhein, Durham, NC (US); Shivanand Lad, Durham, NC (US)

(73) Assignee: Duke University, Durham, NC (US)

( * ) Notice: Subject to any disclaimer, the term of this patent is extended or adjusted under 35 U.S.C. 154(b) by 315 days.

(21) Appl. No.: 16/775,750

(22) Filed: Jan. 29, 2020

(65) Prior Publication Data

US 2020/0238019 A1 Jul. 30, 2020

Related U.S. Application Data

(60) Provisional application No. 62/798,033, filed on Jan. 29, 2019.

(51) Int. Cl.
*A61M 5/32* (2006.01)
*A61M 5/31* (2006.01)
*A61M 5/315* (2006.01)

(52) U.S. Cl.
CPC ........ *A61M 5/3221* (2013.01); *A61M 5/3134* (2013.01); *A61M 5/3135* (2013.01); *A61M 5/31565* (2013.01); *A61M 5/3245* (2013.01); *A61M 2205/0266* (2013.01)

(58) Field of Classification Search
CPC .............. A61M 5/3221; A61M 5/3134; A61M 5/3245; A61M 2205/0266
See application file for complete search history.

(56) References Cited

U.S. PATENT DOCUMENTS

| 6,592,559 | B1* | 7/2003 | Pakter .............. A61B 17/3417 604/272 |
| 8,048,030 | B2 | 11/2011 | McGuckin, Jr. et al. |
| 8,052,661 | B2 | 11/2011 | McGuckin, Jr. et al. |
| 8,747,359 | B2 | 6/2014 | Pakter et al. |
| 8,784,382 | B2 | 7/2014 | McGuckin, Jr. et al. |
| 2009/0177161 | A1 | 7/2009 | McGuckin, Jr. et al. |
| 2009/0326412 | A1 | 12/2009 | Pakter |

(Continued)

FOREIGN PATENT DOCUMENTS

WO 01/41860 A1 6/2001

*Primary Examiner* — Bradley J Osinski
(74) *Attorney, Agent, or Firm* — Olive Law Group, PLLC

(57) ABSTRACT

Medicinal fluid delivery devices and methods for advancing and retracting needles are disclosed. According to an aspect, a medicinal fluid delivery device includes a tube that defines an interior space that extends between a first and second openings. The device includes a needle including a proximal end and a distal end that substantially align in a first direction. A portion of the distal end is biased to extend in a second direction different than the first direction. A mechanism is attached to the proximal end and configured to position the distal end between a first position and a second position. In the first position, the portion of the distal end is constrained by the interior wall such that is does not extend in the second direction. In the second position, the distal end is not constrained by the interior wall such that it extends in the second direction.

16 Claims, 15 Drawing Sheets

(56) References Cited

U.S. PATENT DOCUMENTS

| | | |
|---|---|---|
| 2010/0106093 A1 | 4/2010 | McGuckin, Jr. et al. |
| 2010/0130850 A1 | 5/2010 | Pakter |
| 2012/0046664 A1 | 2/2012 | McGuckin, Jr. et al. |
| 2012/0123427 A1 | 5/2012 | McGuckin, Jr. et al. |
| 2013/0137979 A1* | 5/2013 | Deckman .......... A61B 8/12 |
| | | 600/439 |

* cited by examiner

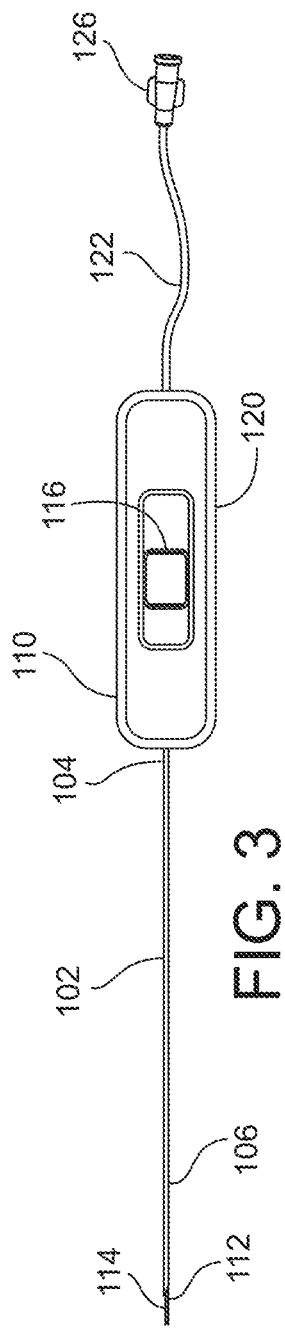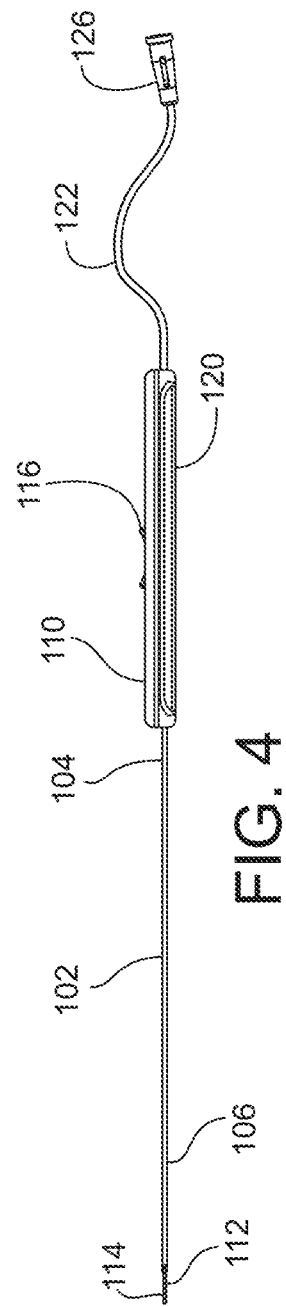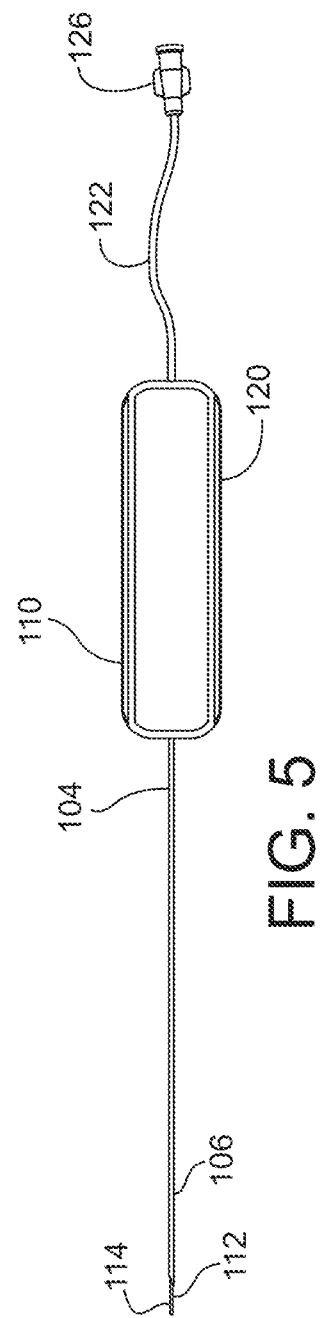

30°

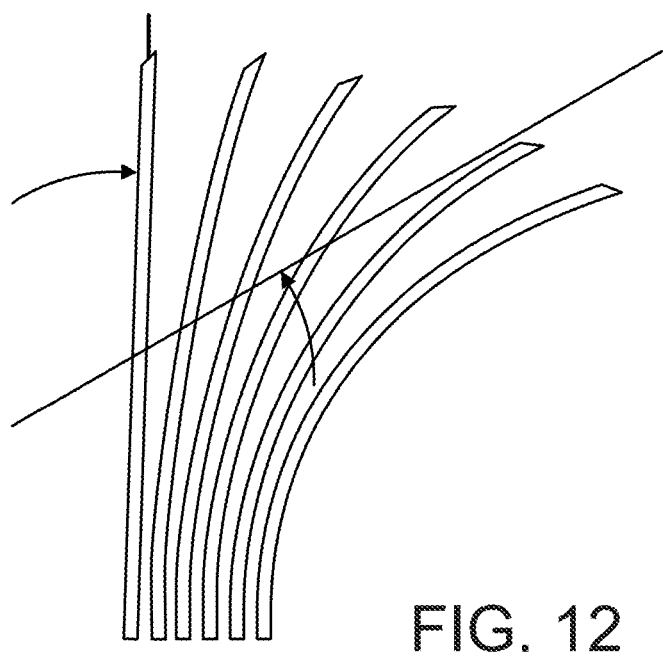
FIG. 12
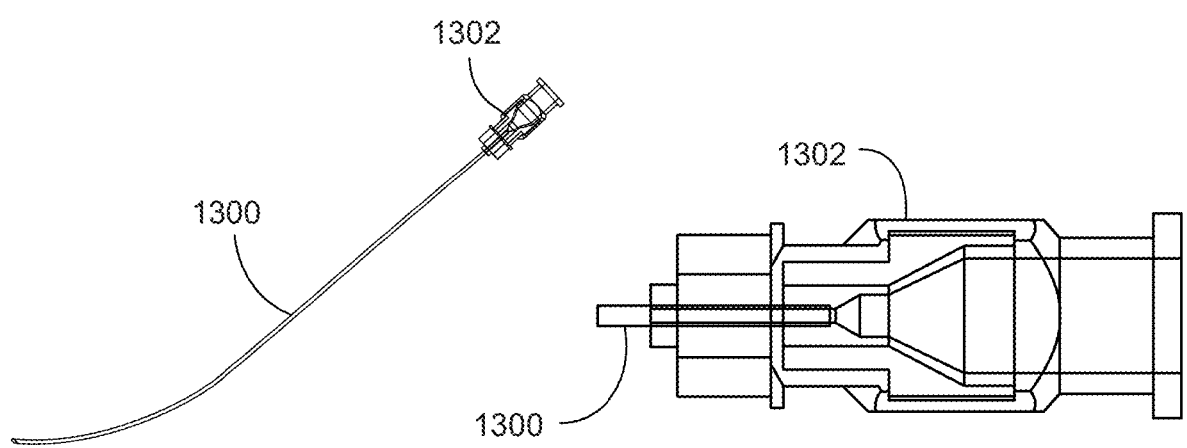
FIG. 13
FIG. 14

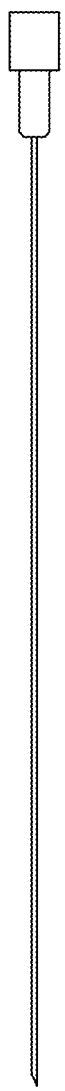
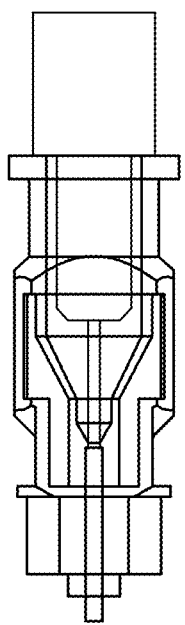
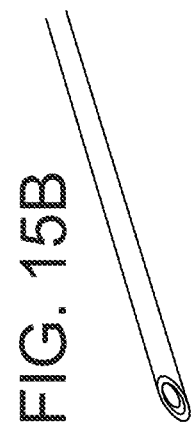
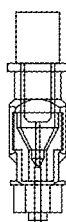
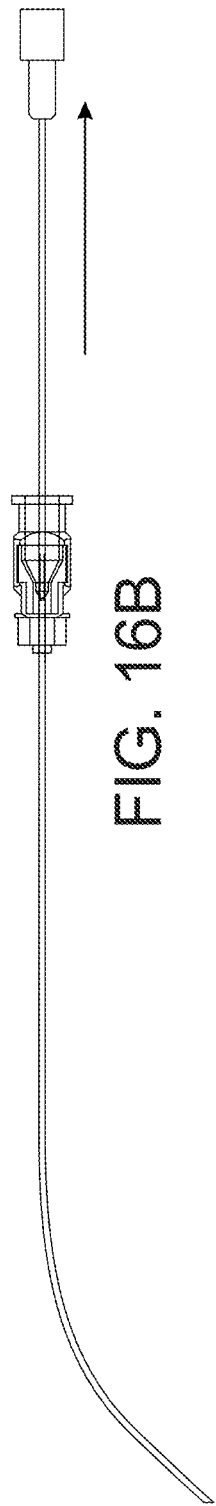
FIG. 15A
FIG. 15B
FIG. 15C
FIG. 16A
FIG. 16B

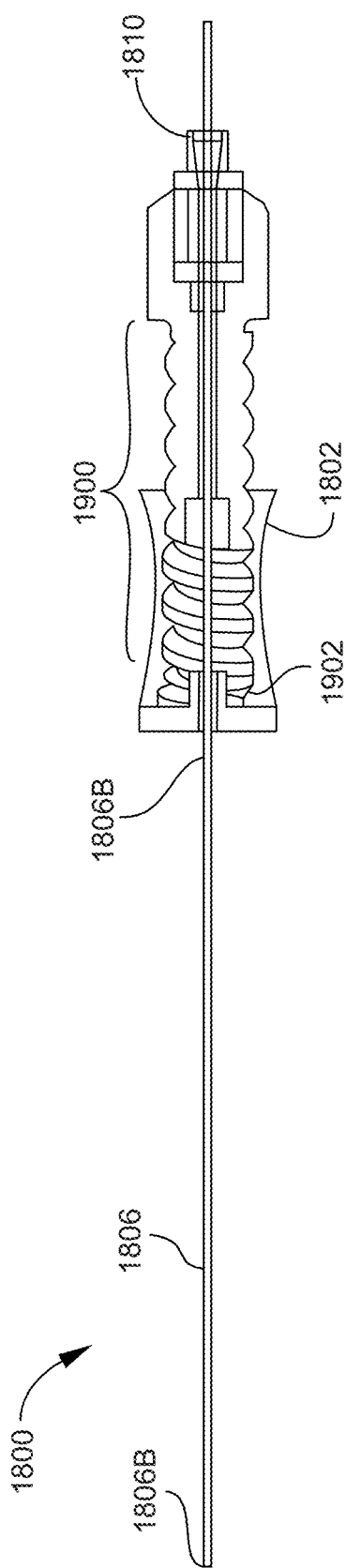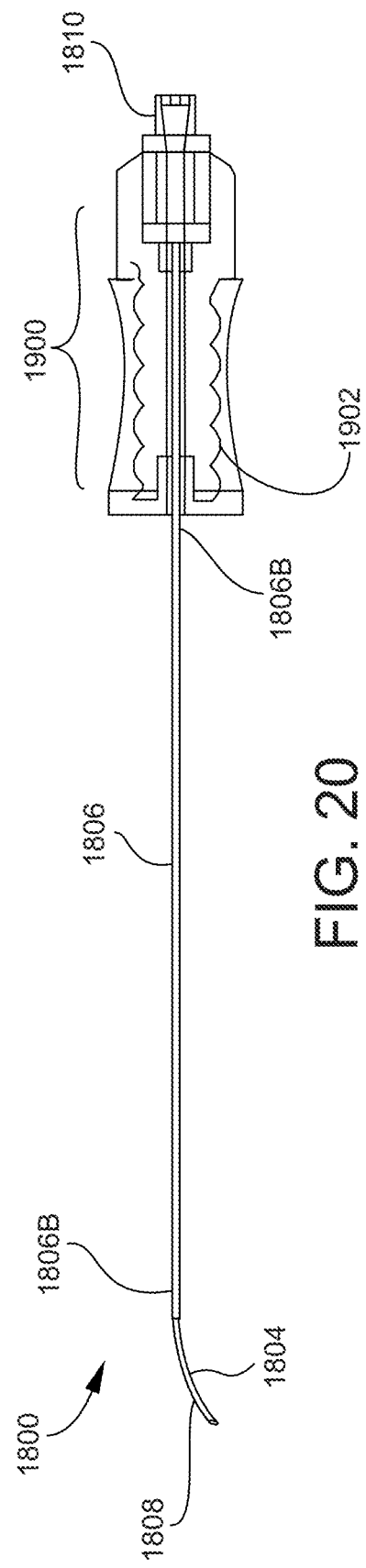
FIG. 19
FIG. 20

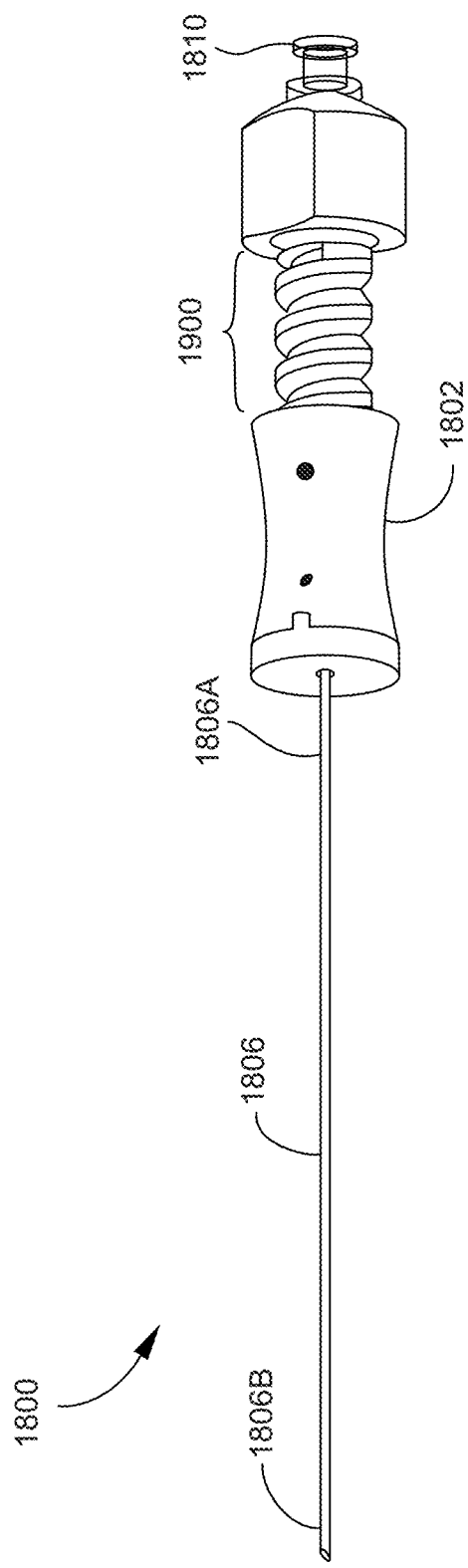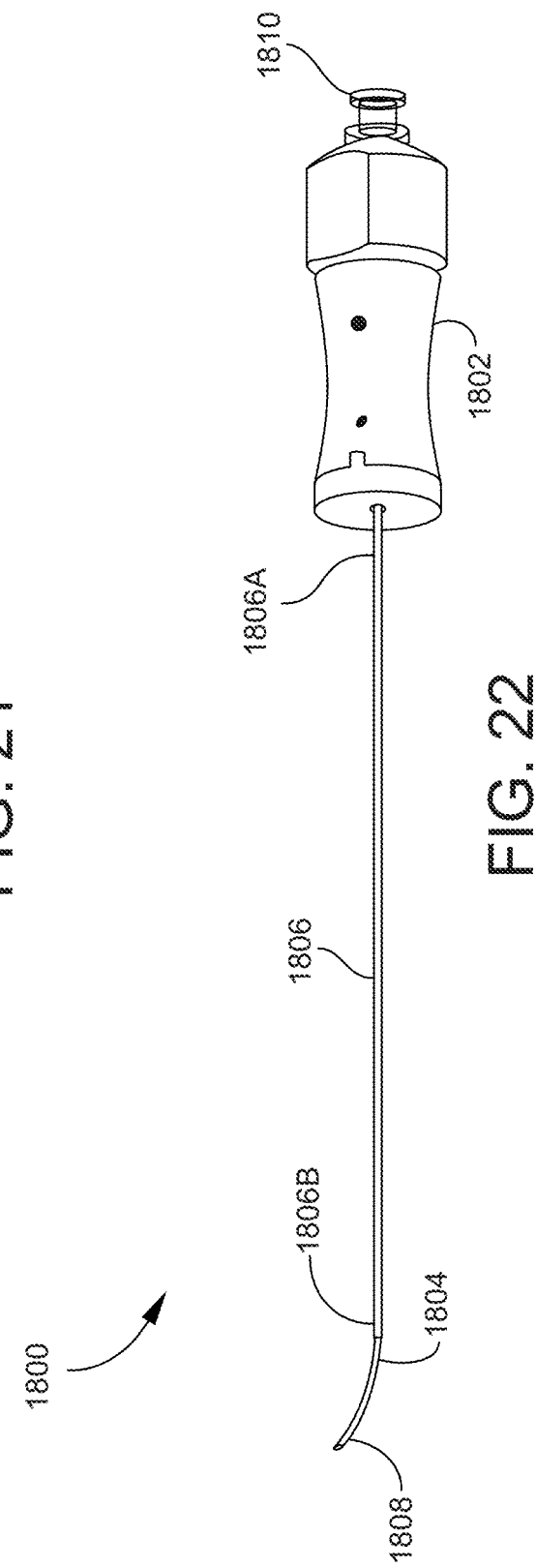

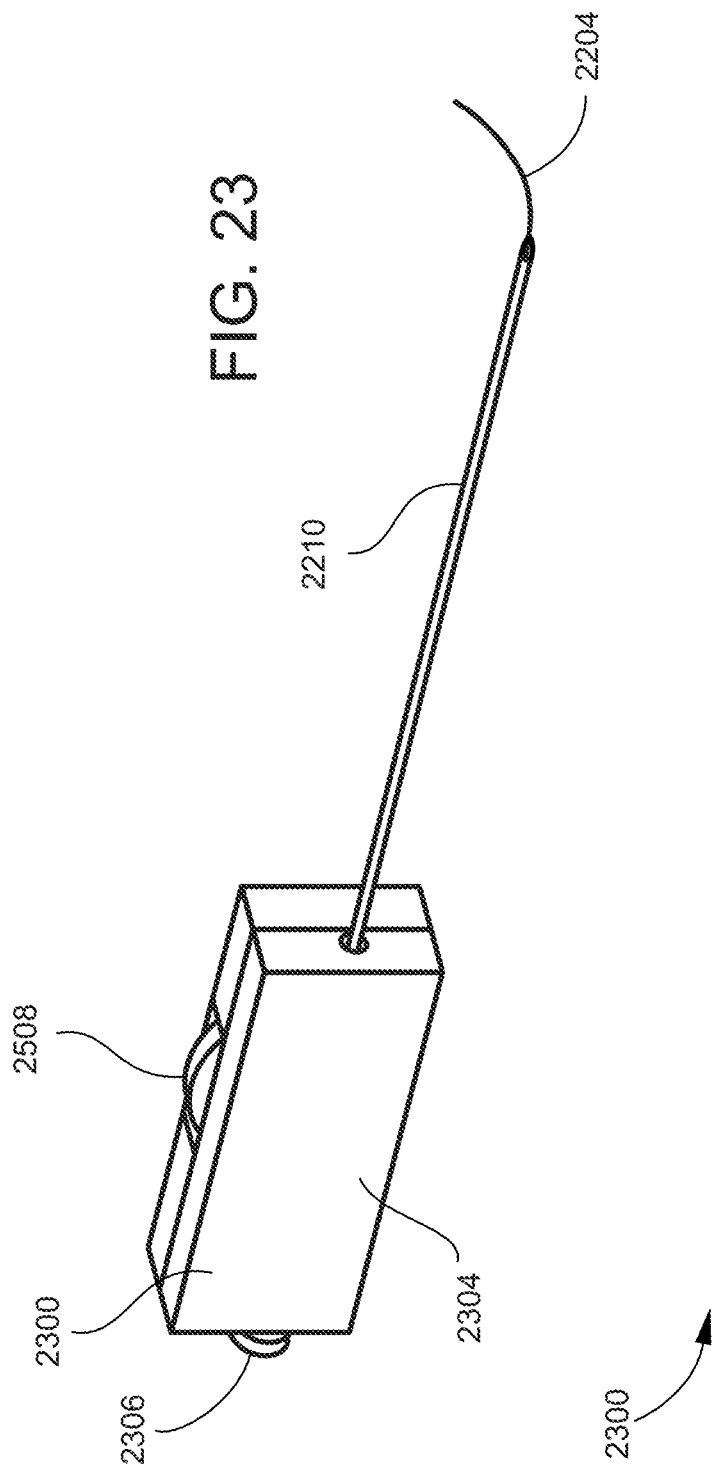
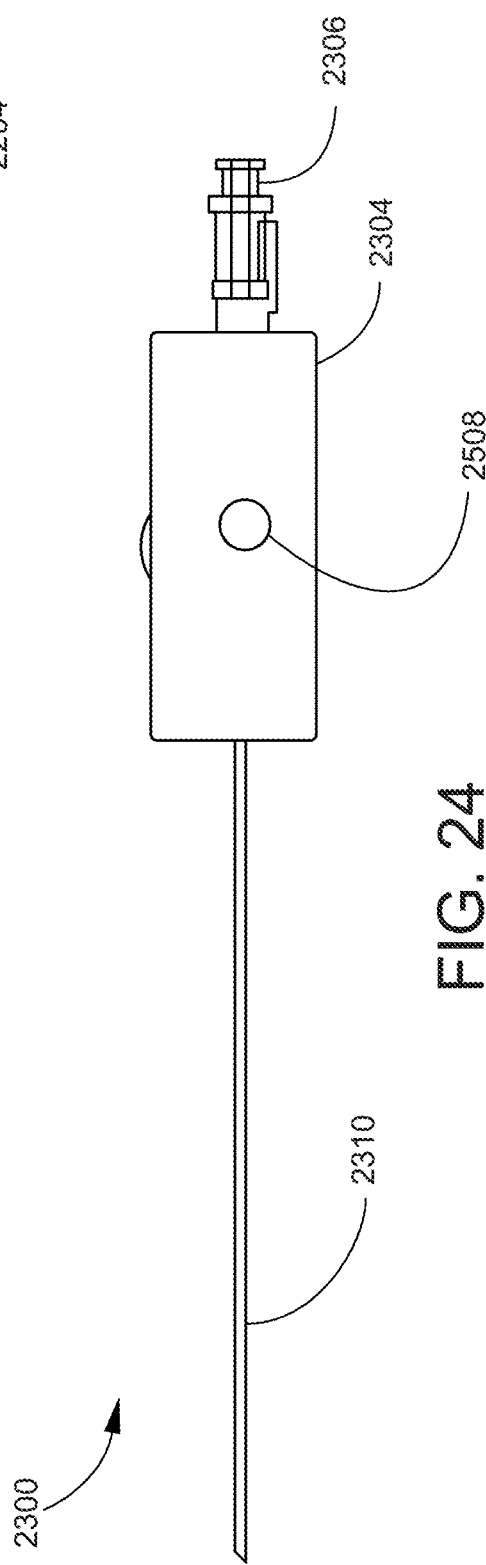

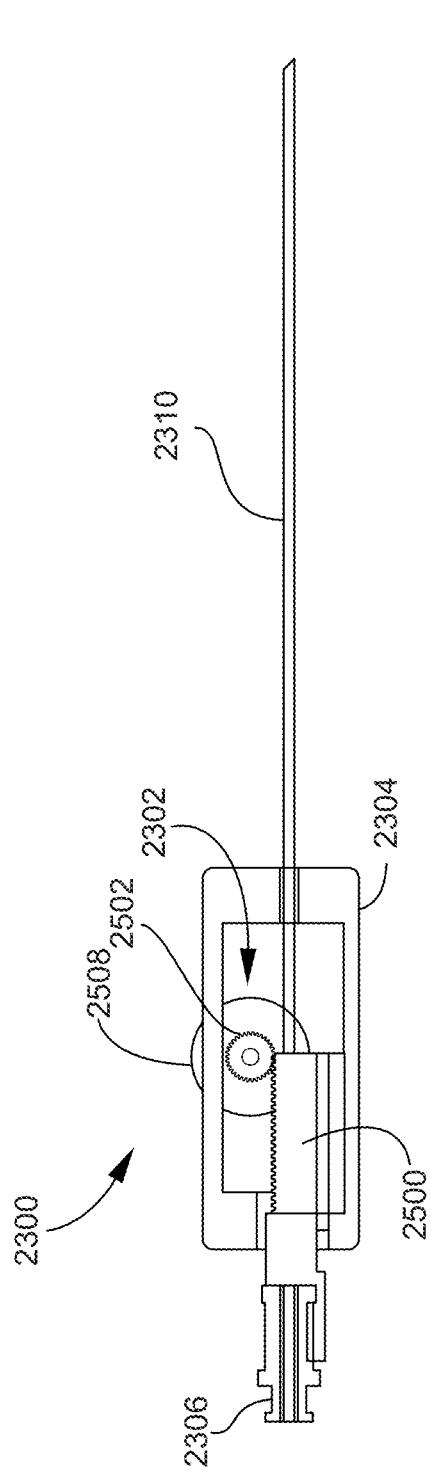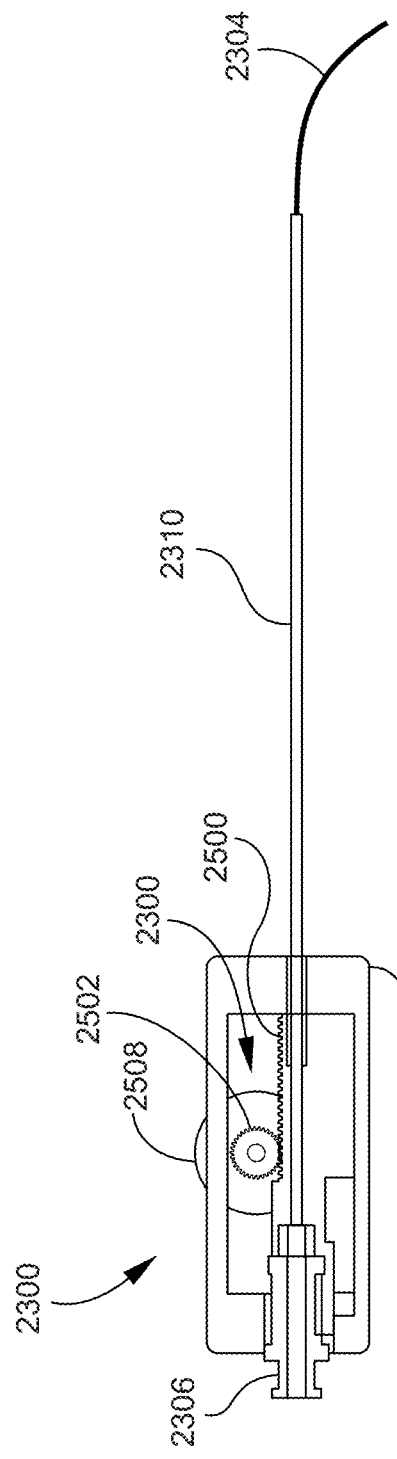

MEDICINAL FLUID DELIVERY DEVICES AND ASSOCIATES METHODS FOR ADVANCING AND RETRACTING NEEDLES

CROSS REFERENCE TO RELATED APPLICATION

This application claims priority to U.S. patent application Ser. No. 62/798,033, filed Jan. 29, 2019, and titled SUBSTRATE DELIVERY DEVICE AND METHODS OF USING SAME, the content of which is incorporated herein by reference in its entirety.

TECHNICAL FIELD

The presently disclosed subject matter relates generally to medical devices and procedures. Particularly, the presently disclosed subject matter relates to medicinal fluid delivery devices and methods for advancing and retracting needles.

BACKGROUND

Spontaneous intracranial hypotension (SIH) affects an estimated 5 in 100,000 people, amounting to over 16,000 cases in the United States annually. Patients with SIH commonly experience orthostatic headaches but have also reported other debilitating symptoms including visual changes, cognitive deficits, and cranial nerve dysfunction. Cerebrospinal fluid (CSF) leaks arising from spinal dural defects are the leading cause of SIH and can occur at various sites ranging from the nerve root sleeves to the ventral dura. Leaks associated with nerve root sleeves are more easily accessed percutaneously for treatment. Conversely, ventral CSF leaks are anatomically challenging to access percutaneously, thus requiring highly skilled interventional treatment.

Epidural blood patch (EBP) is a widely adopted method for treating CSF leaks. This procedure involves injecting autologous blood or a combination of autologous blood and fibrin glue along the dural defect via placement of a needle in the epidural space. The aim of this treatment is to create a durable seal at the CSF leak site and normalize CSF hydrodynamics. While nerve root sleeve CSF leaks can be treated by fluoroscopically guided targeted EBP, ventral dural tears often require targeted EBP by CT fluoroscopic guidance. A recent study assessed success rates for transforaminal delivery of targeted EBPs to ventral dural tears and found that needle position within the spinal canal was critical to achieving optimal contrast spread. Although contrast delivery to the ventral epidural space (VES) was possible in 96% of cases, localization into all three of the ipsilateral, central, and contralateral regions was only achieved in 14% of cases. Precise access to this space is challenging due to the technological limitation of using straight epidural needles within the spatial constraints of the surrounding anatomy, increasing the risks of dural puncture, spinal cord injury, or inadvertent intravascular injection as well as EBP failure. Furthermore, due to the technical expertise required for diagnosing and treating these CSF leaks, very few physicians are capable or qualified to perform ventral EBP. Even at high-volume centers for treating CSF leaks, there is often a 2-3 month backlog of patients awaiting treatment from the limited physicians available to perform this highly specialized procedure. Consequently, there is a need for specialized EBP tools for simplifying the procedure to improve accessibility and enhance patient outcomes.

BRIEF DESCRIPTION OF THE DRAWINGS

Figure 1:
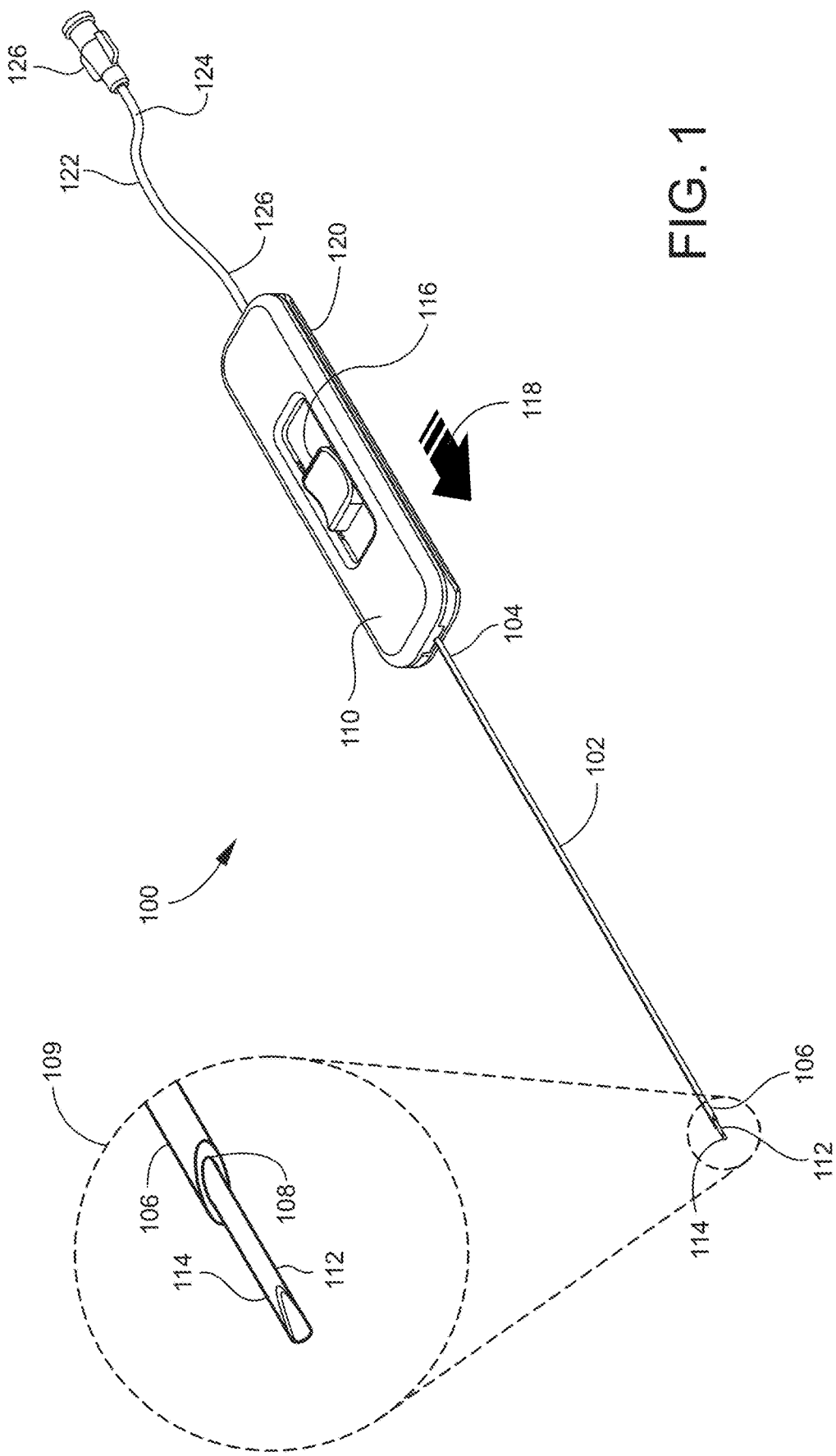
Figure 2:
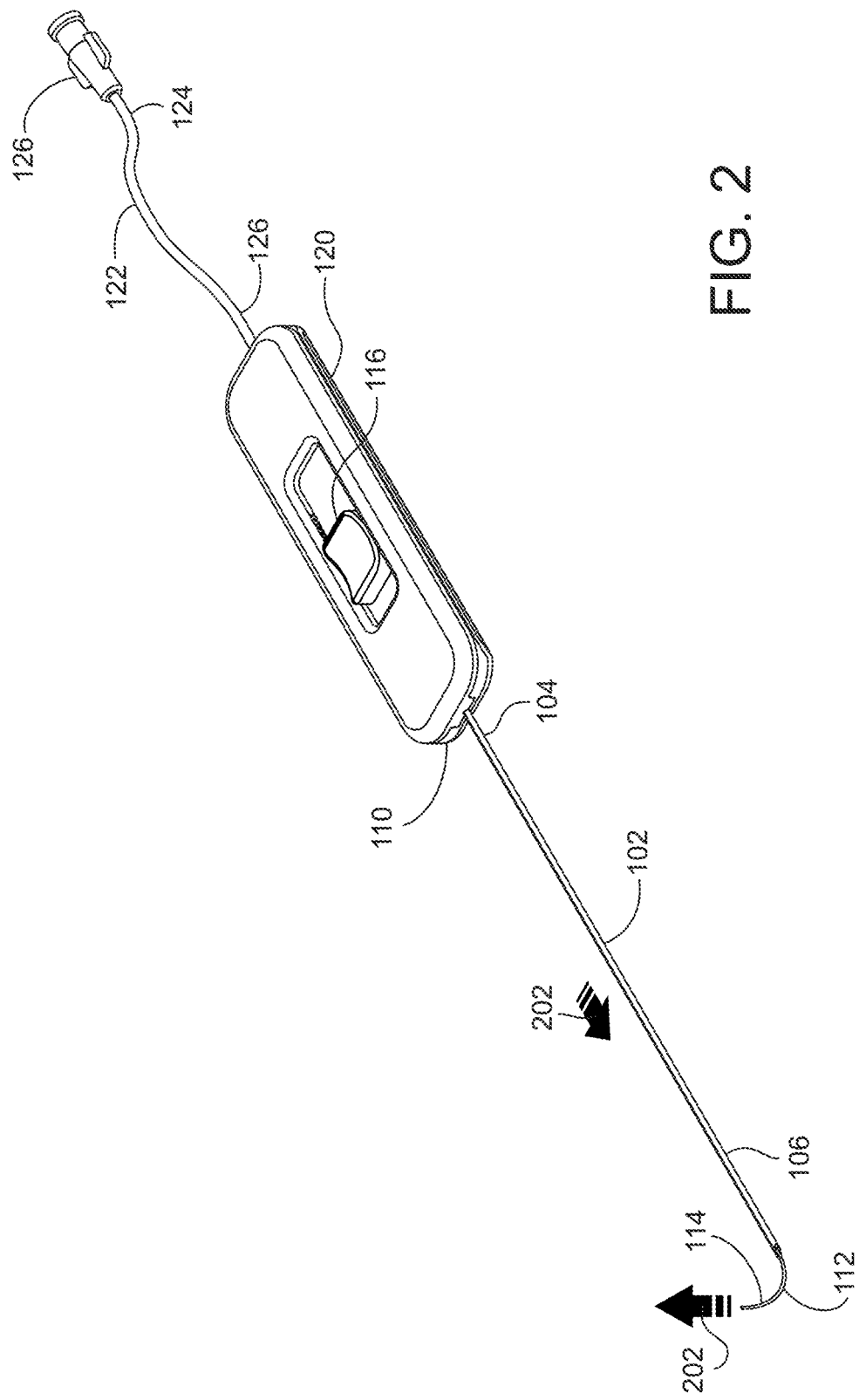
Figure 6:
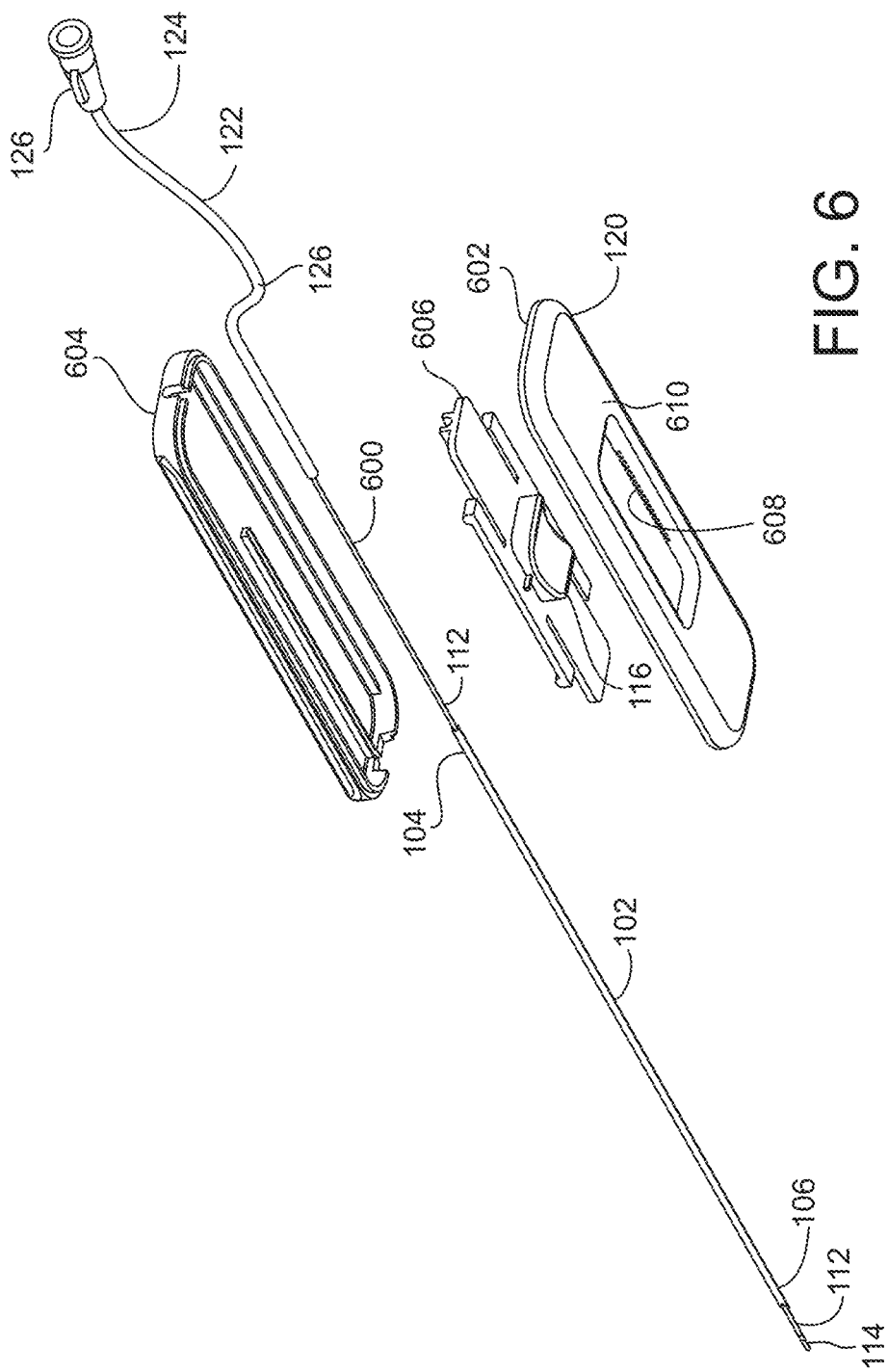
Figure 7:
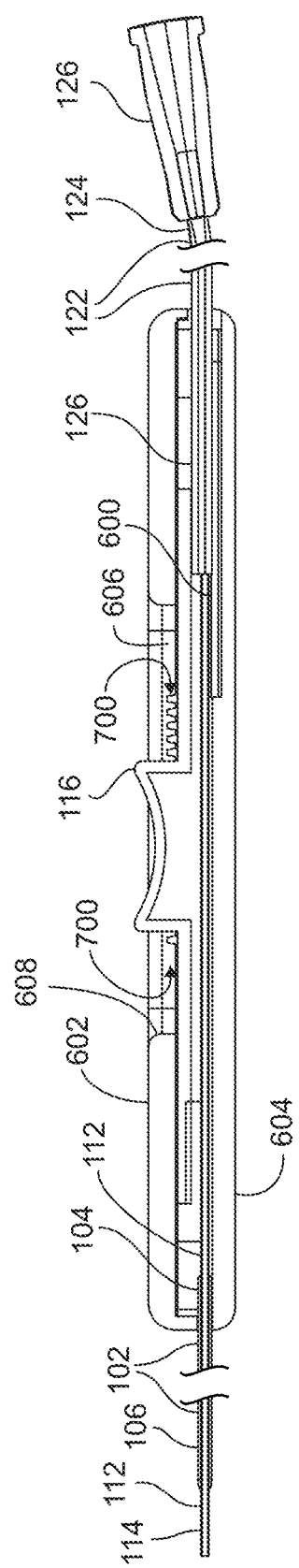
Figure 8:
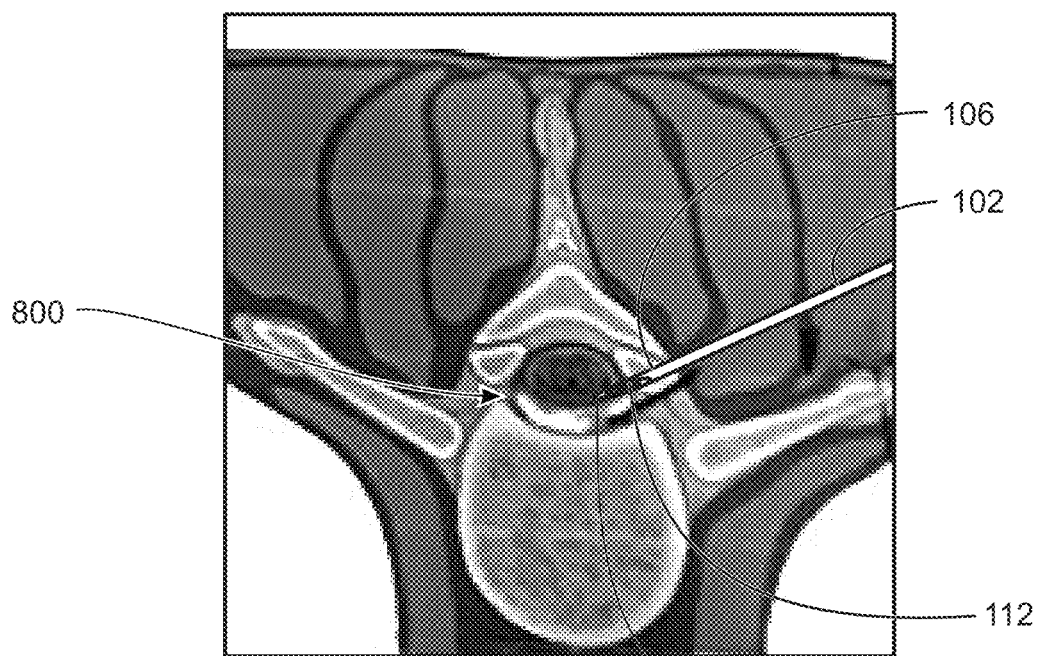
Figure 9:
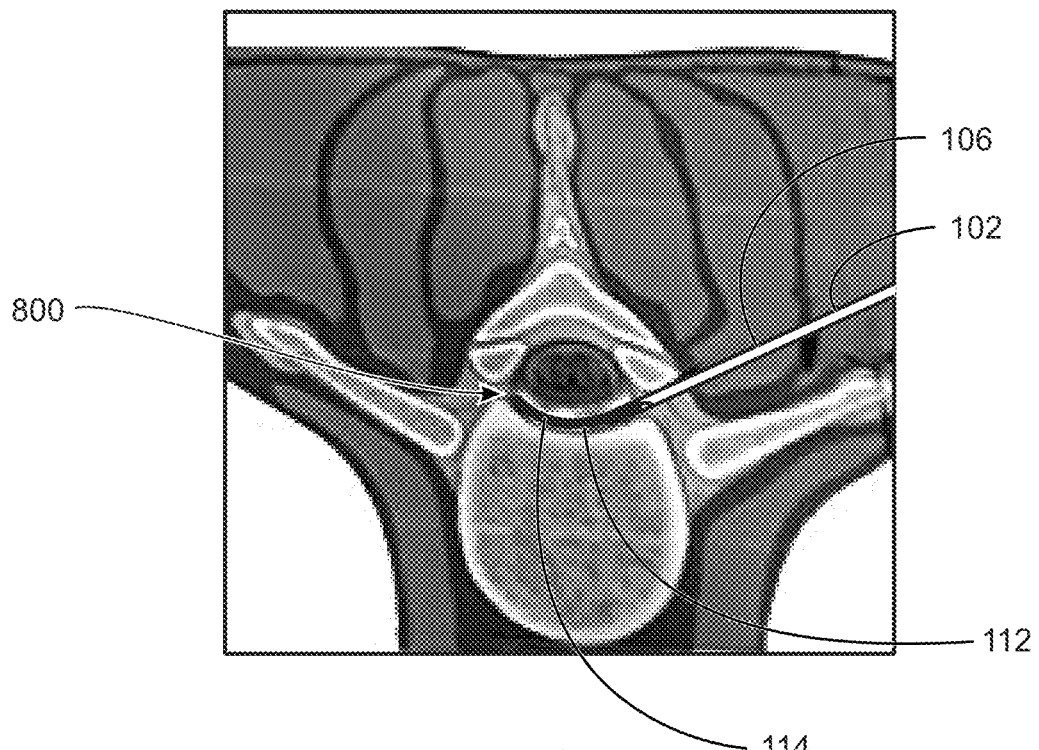
Figure 10:
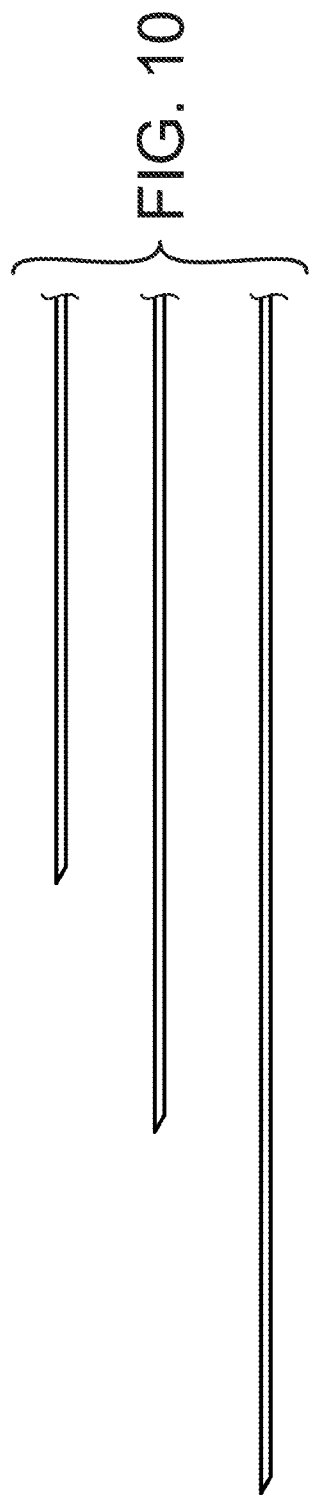
Figure 11:
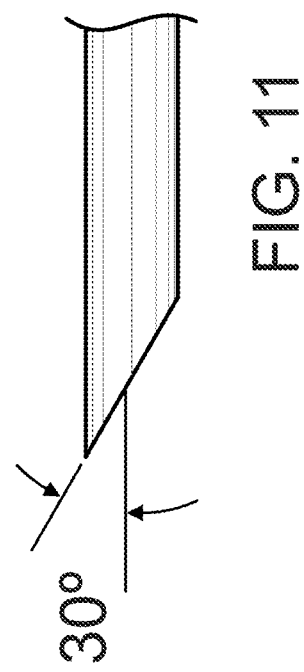
Figure 17A:
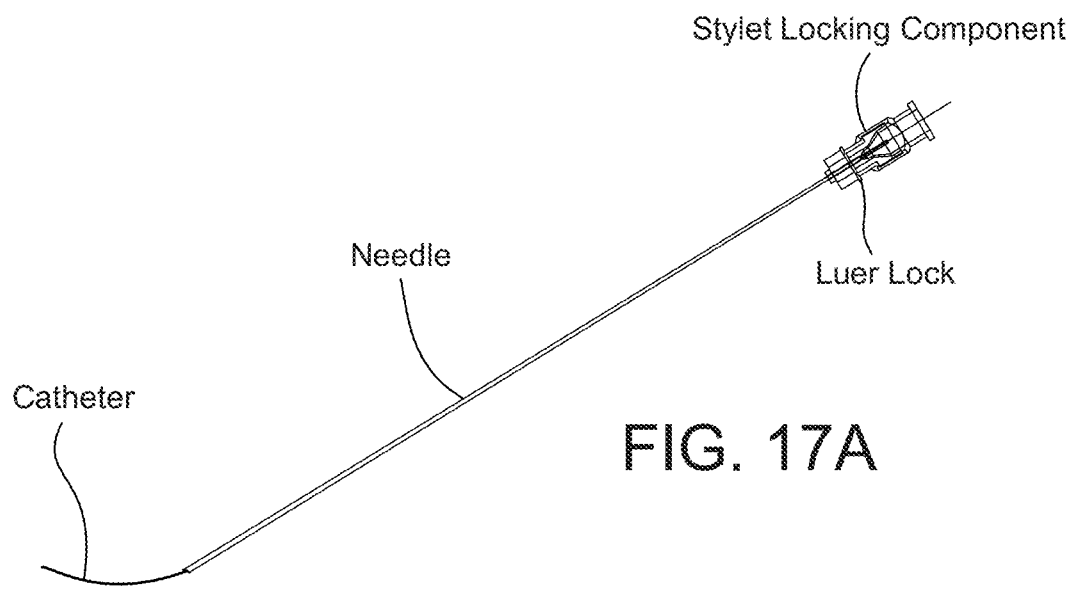
Figure 17B:
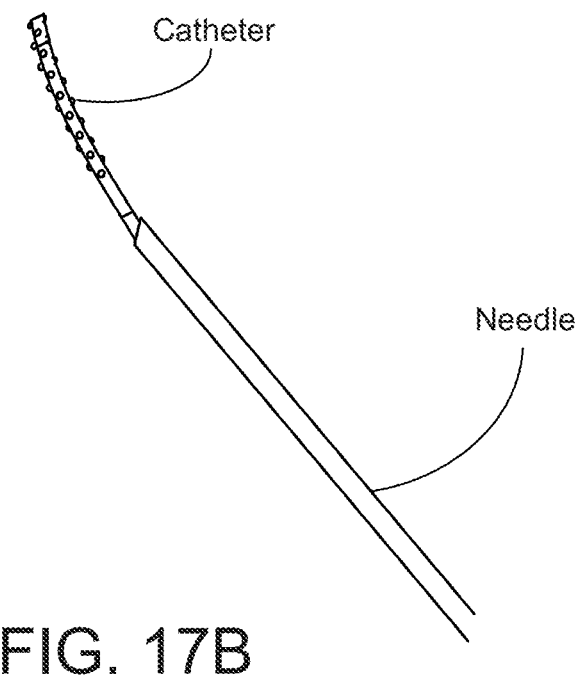
Figure 18:
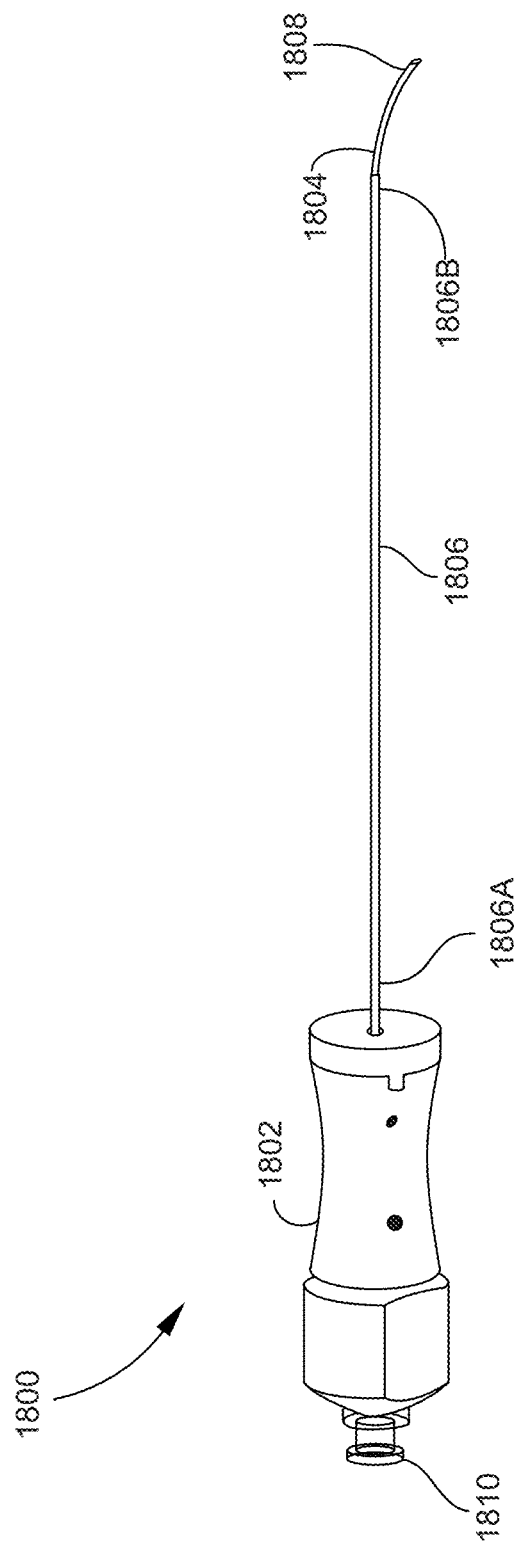

Having thus described the presently disclosed subject matter in general terms, reference will now be made to the accompanying Drawings, which are not necessarily drawn to scale, and wherein:

FIG. 1 is a top view of a medicinal fluid delivery device in accordance with embodiments of the present disclosure;

FIG. 2 is a top view of the medicinal fluid delivery device shown in FIG. 1 with the needle advanced further than the position shown in FIG. 1;

FIGS. 3, 4, and 5 are a top view, a side view, and a bottom view, respectively, of the medicinal fluid delivery device shown in FIGS. 1 and 2;

FIG. 6 is an exploded, perspective view of the medicinal fluid delivery device shown in FIGS. 1-5;

FIG. 7 is a cross-sectional, side view of the medicinal fluid delivery device shown in FIGS. 1-6;

FIGS. 8 and 9 are diagrams that depict example steps using the medicinal fluid delivery device shown in FIGS. 1-7 for delivering medicinal fluid to a target area of a patient in accordance with embodiments of the present disclosure;

FIG. 10 illustrates a side view of needles of different lengths;

FIG. 11 is a zoomed-in side view of a needle tip having a tapered angle of 30°,

FIG. 12 is a side view of a straight needle and curved needles of different curvatures of 0°, 15°, 30°, 45°, 60°, and 75°;

FIG. 13 is a perspective view of a curved needle attached to a Luer lock in accordance with embodiments of the present disclosure;

FIG. 14 is a zoomed-in, cross-sectional view of the curved needle and Luer lock shown in FIG. 13;

FIGS. 15A, 15B, and 15C illustrate a side view, a zoomed-in perspective view, and a cross-sectional side view, respectively, of a stylet attached to a curved needle and Luer lock;

FIGS. 16A and 16B are side views of a needle assembly in a straight configuration and a curved configuration as the stylet has been removed in accordance with embodiments of the present disclosure;

FIG. 17A is a perspective view of a catheter inserted through a needle in accordance with embodiments of the present disclosure;

FIG. 17B is a zoomed-in, perspective view of the needle with the catheter exiting the needle's tip in accordance with embodiments of the present disclosure;

FIG. 18 is a perspective view of a medicinal fluid delivery device having a mechanism that can move a needle (or co-axial delivery tube) between different positions in accordance with embodiments of the present disclosure;

FIG. 19 is a side, cross-sectional, perspective view of the medicinal fluid delivery device shown in FIG. 18 in a retracted position;

FIG. 20 is cross-sectional, side views of the medicinal fluid delivery device shown in FIGS. 18 and 19 in an advanced position in accordance with embodiments of the present disclosure;

FIGS. 21 and 22 illustrate a side, perspective view of the medicinal fluid delivery device shown in FIGS. 18 and 19 in an advanced position and a retracted position, respectively;

FIG. 23 is a perspective view of a medicinal fluid delivery device having a rack-and-pinion mechanism in an extended position in accordance with embodiments of the present disclosure FIG. 24 is a side view of the device shown in FIG. 23 in a retracted position;

FIG. 25 is a cross-sectional side view of the device shown in FIGS. 23 and 24 in a retracted position; and FIG. 26 is a cross-sectional side view of the device shown in FIGS. 23-25 in an extended position.

SUMMARY

The presently disclosed subject matter relates to medicinal fluid delivery devices and methods for advancing and retracting needles. According to an aspect, a medicinal fluid delivery device includes a tube including a first opening and a second opening. The tube defines an interior space that extends between the first opening and the second opening. The interior space has an interior wall. Further, the device includes a needle including a proximal end and a distal end that substantially align in a first direction. A portion of the distal end is biased to extend in a second direction that is different than the first direction. Further, the device includes a mechanism attached to the proximal end of the needle and configured to position the distal end between a first position and a second position. The first position the distal end is within the interior space. In the first position, the portion of the distal end is constrained by the interior wall such that is does not extend in the second direction. In the second position the distal end is outside the interior space such that the portion of the distal end is not constrained by the interior wall such that it extends in the second direction.

According to another aspect, a medicinal fluid delivery device includes a tube including a first opening and a second opening. The tube defines an interior space that extends between the first opening and the second opening. The interior space has an interior wall. The device also includes a needle including a proximal end and a distal end that substantially align in a first direction. A portion of the distal end is biased to extend in a second direction that is different than the first direction wherein the portion of the distal end is made of shape-memory material. The portion of the distal end is made of shape-memory material. The distal end of the needle is positionable between a first position and a second position. In the first position, the distal end is within the interior space and the portion of the distal end is constrained by the interior wall such that is does not extend in the second direction. In the second position, the distal end is outside the interior space such that the portion of the distal end is not constrained by the interior wall such that it extends in the second direction.

According to another aspect, a method of medicinal fluid delivery includes providing a medicinal fluid delivery device. The device includes a tube including a first opening and a second opening. The tube defines an interior space that extends between the first opening and the second opening. The interior space has an interior wall. Further, the device includes a needle including a proximal end and a distal end that substantially align in a first direction. A portion of the distal end is biased to extend in a second direction that is different than the first direction. The method includes moving the needle between a first position and a second position. In the first position, the distal end is within the interior space and the portion of the distal end is constrained by the interior wall such that is does not extend in the second direction. In the second position, the distal end is outside the interior space such that the portion of the distal end is not constrained by the interior wall such that it extends in the second direction.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As referred to herein, the term "medicinal fluid" refers generally to any fluid containing medicine used in treating disease or illness. As an example, medicinal fluid may include steroids or stem cells for the treatment of chronic pain. Other example medicinal fluids include, but are not limited to, dexamethasone, triamcinolone, methylprednisolone, and betamethasone acetate.

As referred to herein, the term "tube" is generally any elongated body having an opening at each end and an interior space that extends between the openings. The body of the tube may be rigid or substantially rigid. In an example, the body of the tube may be cylindrical or substantially cylindrical in shape. Alternatively, for example, the body of the tube may have another shape with squared or angled edges along its length. The tube may be part of a medicinal fluid delivery device for holding a needle as disclosed herein. Particularly, the tube may be used for holding a needle and for guiding the needle's tip end to a target area within a subject (i.e., a patient) for delivery of medicinal fluid. During the procedure for placement of the needle's tip end to the target area, the needle's tip end and its shaft may be held entirely or at least partially within the tube. Once positioned at or near the target area for delivery of medicinal fluid, the needle may be moved forwarded and otherwise adjusted such that the needle's tip is at a desired location for release of the fluid from the tip.

As referred to herein, the term "needle" is generally any medical tool that is a tube with a sharp-tipped end having an opening. The needle may be used with a syringe to inject medicinal fluid or other fluid substances into the body or to extract fluid from the body. Generally, the needle may have an elongated body (often referred to as a "shaft") that defines an interior space extending between its two ends, which may be referred to as a "proximal end" and a "distal end". At the proximal end, the needle may be attached to the syringe or other device or component suitable for holding the proximal end. The distal end may be sharply shaped or beveled in shape to define a point or tip. In another example, the delivery needle or tube may be blunt or rounded. In the ventral EBP indication, the tip may not be sharpened. The introducer needle may have a sharp or beveled tip. The interior space within the elongated body, or shaft, is often referred to as the lumen. The needle may be made of metal or another rigid substance. In accordance with embodiments of the present disclosure, the needle may be made of shape-memory material such as, but not limited to, an alloy of nickel-titanium (often referred to as "Nitinol"), copper-aluminum-nickel, or the like. As described in more detailed herein, the proximal and distal ends of the needle may be generally in alignment but the distal end may, when not mechanically constrained, extend in a different direction. For example, the distal end may have a curved or other shape such that it extends in one or more other directions than the needle's shaft. This shape may be formed in this way such that needle's tip may be maneuvered around structures (e.g., bone or critical body tissue) within the patient's body for placement of the needle's tip to a target area. As an example, an angle measurement between the alignment of the shaft of the needle and the distal end may be between about 15 degrees and about 75 degrees.

FIG. 1 illustrates a top view of a medicinal fluid delivery device 100 in accordance with embodiments of the present disclosure. Referring to FIG. 1, the device 100 includes an elongated tube 102 having a proximal end 104 and an opposing distal end 106. In this example, the tube 102 is slender and cylindrical in shape; however, it should be understood that the tube 102 may alternatively be of any suitable shape and size. The length of the tube 102 may be between approximately 3.5 inches and approximately 6 inches. The width of the tube 102 may be between approximately 17 G and approximately 23 G.

The tube 102 defines an interior space (not shown in FIG. 1) that extends between an opening (not shown in FIG. 1) at the proximal end 104 and an opening, generally designated 108 and shown in the zoomed in portion shown in the broken line circle 109, at the distal end 106. The proximal end 104 may be attached to a mechanism 110 that may be used by an operator to advance or retract a needle 112. Some or all of the needle 112 may be held within the interior space of the tube 102. In the view of FIG. 1, most of the needle 112 is positioned within the interior space of the tube 102, and a portion of a distal end 114 of the needle 112 is outside of the tube 102. Particularly, the distal end 114 extends outside the opening 108 of the needle 112, and such positioning of the need may be user-selected based on a user's operation of the mechanism 110 as will be described in more detail herein.

The mechanism 110 is attached to a proximal end (not shown in FIG. 1) of the needle 112. Further, the mechanism 110 can move forward the needle 112 through the tube 102 such that the distal end 112 extends outside of the tube 102 as shown in FIG. 1 and to other positions extends from the opening 108. The mechanism 110 can also retract the needle 112 through the tube 102 such a smaller portion of the distal end 114 is outside the opening or such that the entirety of the needle 112 is within the tube 102. A user may control such operation by use of a slider 116 or other component that may be manipulated for advancing or for retracting the needle 112. In this example, the slider 116 may be moved in the direction of arrow 118 for advancing the needle 112. Further, for example, the slider 116 may be moved in a direction opposing arrow 118 for retracting the needle 112. The mechanism 110 may include a housing 120 for holding components for advancing and retracting the needle 112 by use of the slider 116.

Within continuing reference to FIG. 1, the mechanism 110 may be connected to a flexible tube 122. The tube 122 has an end 124 for receipt of medicinal fluid into the tube 112. The end 124 may have a Luer connector 126 or another suitable connector configured to operatively connect to a syringe (not shown) for controlled input of the medicinal fluid into the needle 112 as will be understood by those of skill in the art. An opposing end 126 of the tube 122 may be connected to the mechanism 110 for transport of the medicinal fluid through the mechanism 110 and into the needle 112 for delivery to a target area of a subject.

FIG. 2 illustrates a top view of the medicinal fluid delivery device 100 shown in FIG. 1 with the needle 112 advanced further than the position shown in FIG. 1. Referring to FIG. 2, more of the distal end 114 of the needle 112 is outside of the tube 102 than shown in FIG. 1. This is because the mechanism 110 has advanced the needle 112 further forward than in FIG. 1. The slider 116 can be moved in the forward direction to advance the needle 112 forward to the position shown in FIG. 2 from the position shown in FIG. 1.

With continuing reference to FIG. 2, the distal end 114 of the needle 112 is shown as being curved in shape such that its tip extends in a direction different than the alignment of the tube 102. Particularly, the tip of the distal end 114 points in a direction generally indicated by arrow 200 while the tube 102 (and thereby the length of the needle 112 held therein) extends in a direction generally indicated by arrow 202. It is noted that the direction of arrow 202 substantially aligns with the portion of the needle 112 held within the interior space of the tube 102 because the position of the needle within the interior space is mechanically constrained by the wall(s) formed by the interior space of the tube 102.

As described and shown in FIG. 2, the distal end 114 of the needle 112 is curved in shape. This is because the needle 112 is made of shape-memory material. For example, the needle 112 may be made of an alloy of nickel-titanium or Nitinol and curved in shape as shown in FIG. 2 when it is mechanically unconstrained. When all or a sufficient portion of the distal end 114 is retracted into the tube 102, the distal end 114 becomes mechanically constrained by the walls of the tube's 102 interior such that the distal end 114 substantially straightens. When the distal end 114 is advanced, the constraints of the interior wall of the tube 102 are reduced such that the distal end 112 gradually returns to its natural curved shape.

FIGS. 3, 4, and 5 illustrate a top view, a side view, and a bottom view, respectively, of the medicinal fluid delivery device 100 shown in FIGS. 1 and 2. In the views of FIGS. 3, 4, and 5, the needle 112 is shown positioned in a retracted position such that most of the needle 112 is within the tube and such that the distal end 114 is straightened due to its mechanical constraint by the interior wall(s) of the tube 102.

FIG. 6 illustrates an exploded, perspective view of the medicinal fluid delivery device 100 shown in FIGS. 1-5. Referring to FIG. 6, the figure shows that a distal end 600 of the needle 112 is fluidly attached to the end 126 of the tube 122 to thereby provide for passage of medicinal fluid input at the Luer connector 126 to the distal end 114 of the needle 112 for delivery to a target location. As shown, a portion of the distal end 600 extends outside of the end 104 of the tube 102 and can be held within the housing 120 of the mechanism 110.

The housing 120 includes a top portion 602 and a bottom portion 604 that can be attached together to form the housing 120 shown in FIGS. 1-5. The housing 120 hold and contain the proximal end 600 of the needle 112, the end 104 of the tube 102, and the end 126 of the tube 122. Further, the slider 116 may be attached to a needle-engagement portion 606 that can mechanically engage the proximal end 600 of the needle 112 when assembled as shown in FIGS. 1-5 such that the needle 112 is advanced or retracted in response to the slider 116 being moved. The top portion 602 of the housing 120 defines a window 608 such that the slider 116 can fit therein.

FIG. 7 illustrates a cross-sectional, side view of the medicinal fluid delivery device 100 shown in FIGS. 1-6. Referring to FIG. 7, the center portions of the tube 102 (and portion of the needle 112 therein) and the tube 122 are depicted as being shortened for convenience of illustration such that other portions of the device 100 are more easily seen. Further, in this cross-sectional view a passageway for the flow of medicinal fluid from the Luer connector 126 to the distal end 114 of the needle 112 can be seen. The passageway in this depiction is substantially straight in shape, although it is noted that the passageway but may alternatively be any other suitable shape and size.

With continuing reference to FIG. 7, notches, generally depicted 700, are formed in the top portion 602 of the housing for engaging a mating portion of the needle-engagement portion 606. The notches 700 may alternatively be integrated into any other portion of the mechanism 110. The notches 700 serve to provide controlled advancement and retraction of the needle 112. Particularly, the mating portion of the needle-engagement portion 606 may engage the notches 700 such that the needle 112 can move in a lock-step fashion as a user either moves the slider 116 forward or backward to advance or retract the needle 112. It is noted that in order to disengage the mating portion, the user can press down on slider 116, so that the notch on the side of the slider disengages from the window 608 for providing a "safety mechanism". As a result, controlled and precise advancement of the distal end 114 of the needle 112 can be provided to an operator for controlled and precise placement of the tip of the needle 112 to a target area of a patient for delivery of medicinal fluid. Also, as a result, unintended movement may be prevented that could occur when a user attaches a syringe or other equipment to the Luer connector.

FIGS. 8 and 9 are diagrams that depict example steps using the medicinal fluid delivery device 100 shown in FIGS. 1-7 for delivering medicinal fluid to a target area 800 of a patient in accordance with embodiments of the present disclosure. The diagrams of FIGS. 8 and 9 show a cross-sectional, top view of an anatomy of a subject. Particularly, FIG. 8 shows a transforaminal approach, where the user targets the epidural space just caudad to the inferior margin of the pedicle, immediately superior and lateral to the exiting nerve. FIG. 9 shows the needle 112 passing by the inferior margin of the pedicle and superior to the exiting nerve root sleeve/dural sleeve, allowing the user to access the midline/ventral epidural space. The curve of the needle 112 follows the curvature of the spinal cord and dura surrounding the spinal cord such that the dura is not damaged. For ease of illustration, these diagrams show only the distal end 106 of the tube 102 and the distal end 114 of the needle 112.

Particularly, FIG. 8 shows a step once the distal end 106 of the tube 102 has been inserted to a location where the needle 112 can be advanced for placement of its tip at a target location for delivery of medicinal fluid. Subsequently, as shown in FIG. 9, the needle 112 is advanced such that its distal end 114 moves forward towards the target location. The distal end 114, due to it being advanced and not mechanically constrained by the tube 102, returns to its curved shape such that it can turn about a feature of the patient's anatomy to reach the target location. Once it is verified that the tip of the needle 112 is at the target location, a syringe containing the medicinal fluid can be used to advance the medicinal fluid to the needle 112 such that the medicinal fluid exits the tip at the target location.

In accordance with embodiments, a needle length may be in the range of between about 3.5" and about 7". While in its initial configuration, the needle is straight, with this position lockably maintained. For example, FIG. 10 illustrates a side view of needles (or tubes) of different lengths that function as an introducer for a curved needle as described herein. The lengths are 3.5", 5", and 7". In example, the shaft of the needle can tubular, with an outer diameter of 0.9 mm and an inner diameter of 0.6 mm. The tip of the needle can have a taper with and angle of 30° from the central axis of the needle, or any other suitable shape or angle. As an example, FIG. 11 illustrates a zoomed-in side view of a needle tip having a tapered angle of 30°. The needle may be made of superelastic Nitinol with a transformation temperature sufficiently below room temperature such that it maintains its superelastic properties during normal use and storage.

Once the locking component is removed, the needle can be advanced to return to a curved shape which was heat set into the Nitinol needle. In this configuration, the needle can have a constant ratios curvature with the central axis at the tip having an angle relative to the initial position ranging from 15° to 75°, as shown in FIG. 12, which illustrates a side view of a straight needle and curved needles of different curvatures of 0°, 15°, 30°, 45°, 60°, and 75°. For the purpose of ventral EBP deliveries, the curved needle may not be beveled but rather another suitable shape.

In embodiments, the needle can be attached to a Luer lock by a tight tolerance interference fit and/or a biocompatible adhesive. The lock can be configured to provide a fluid tight seal with a standard medical syringe. The Luer lock can include an attachment for the needle, a central hole for fluid flow, and a locking component for interface with the syringe. FIG. 13 illustrates a perspective view of a curved needle 1300 attached to a Luer lock 1302 in accordance with embodiments of the present disclosure. FIG. 14 illustrates a zoomed-in, cross-sectional view of the curved needle 1300 and Luer lock 1302 shown in FIG. 13. The locking component can be made of a biocompatible plastic. Further, the locking component can be approximately 20 mm in length, with 4.2 mm hole for the syringe to interface with.

In accordance with embodiments, FIGS. 15A, 15B, and 15C illustrate a side view, a zoomed-in perspective view, and a cross-sectional side view, respectively, of a stylet attached to a curved needle and Luer lock. Referring to FIGS. 15A, 15B, and 15C, the stylet can include two components: a wire and a plastic component for attaching to the Luer lock. The wire may be a cylinder of steel wire, with an outer diameter of 0.6 mm. The wire can have a length and taper such that, when inserted fully through the Luer lock and needle, the tapers of the needle and wire are flush with each other. Referring to FIG. 15B, the figure shows the tip of the needle, with wire visible inside. FIG. 15C shows the Luer lock and stylet interface, showing the locking of the stylet in place and the passing of the wire thought the Luer lock.

In accordance with embodiments, the wire can be curved in shape in such a way that when inserted into the needle, the forces that the needle and wire exert on each other cause the needle to remain in its initial straightened configuration. For example, FIGS. 16A and 16B are side views of a needle assembly in a straight configuration and a curved configuration as the stylet has been removed in accordance with embodiments of the present disclosure. Thus, once the stylet is removed or reversed, the force is released and the needle returns to its curved configuration.

The needle may be sized in such a way that in a scenario in which additional extension is required in order to reach the target location or site, a catheter can be inserted through the needle after the removal of the stylet. The patching material can then be applied to the site through the catheter. For example, FIG. 17A illustrates a perspective view of a catheter inserted through a needle in accordance with embodiments of the present disclosure. FIG. 17B illustrates a zoomed-in, perspective view of the needle with the catheter exiting the needle's tip in accordance with embodiments of the present disclosure.

In an example use scenario, a medicinal fluid delivery device in accordance with embodiments of the present disclosure may be inserted into tissue of a patient in a straight configuration and then may advance the needle (or cannula) to target anatomy or a target location that may be difficult to access with a straight epidural needle. In embodiments, the needle or inner cannula may be made of a superelastic Nitinol or another shape-memory material that is heat-set to a desired or predefined curve as disclosed herein. The housing of the device can be sufficiently light such that that the needle does not deflect when placed in tissue. Once the device is positioned in the tissue, the user can press down and slide the actuator (or slider described as being part of the mechanism) to advance the inner cannula. In embodiments, this is a two-part press down and slide motion acts as a safety mechanism to prevent unintentional advancement of the inner cannula or needle. A syringe may be attached to the integrated pigtail to facilitate injection into tissue. In some embodiments, the inner cannula or needle may contain a radiopaque band marker to enhance the radiopacity of the distal tip—especially under C-Arm.

In accordance with embodiments, a medicinal fluid delivery device as disclosed herein can allows the operator fine control to accurately deliver medicinal fluid or a substrate (e.g., stem cells, drug, biologic material, etc.) to a target location, or target tissue for example. As an example, FIGS. 18 and 19 illustrate a perspective view and a side, cross-sectional, perspective view of an example medicinal fluid delivery device 1800 having a mechanism 1802 that can move a needle (or co-axial delivery tube) 1804 between different positions in accordance with embodiments of the present disclosure. Referring to FIGS. 18 and 19, the device 1800 includes a first co-axial introducer tube 1806 having a proximal end 1806A and a distal end 1806B. The second co-axial delivery tube 1804 includes a proximal end (not shown due to being inside the tube 1806 and/or the mechanism 1802) and a distal end 1808. The second co-axial delivery tube 1804 is positioned within the first co-axial introducer tube 1806 and is capable of being extended or advanced beyond the distal end 1806B of tube 1806 by the mechanism 1802. It is noted that the end 1808 of the tube 1804 is shaped to have predefined curvature as shown.

The tube 1806 may be made of any biologically compatible material that is sufficiently strong to allow the tube 1806 to maintain a straight insertion pathway despite housing the curved delivery tube 1804 within. Example materials include, but are not limited to, titanium, stainless steel, gold, and the like.

In accordance with embodiments, the distal end 1806B may be shaped as a beveled end to aid in the insertion of the introducer tube into a subject.

The tube 1804 may be made of any biocompatible material that is flexible and can return to a predetermined shape when bent. Example material includes, but is not limited to, Nitinol or a nylon braid. An exemplary material includes super elastic Nitinol. In such embodiments comprising Nitinol, the tube 1804 may be heat-set at any suitable degree and radius of curvature. In other embodiments, the distal end 1808 may be covered in a polyurethane or other atraumatic material. In some examples, the tubes 1804 and/or 1806 may have a degree of radiopacity such that the user can note the location of the distal tip under C-arm and CT.

With continuing reference to FIG. 18, the device 1800 includes the mechanism 1802 for use by an operator to advance and retract the tube 104. In other embodiments, the device 1800 also include a nozzle 1810 or other suitable component configured to attach the device 1800 to Luer or syringe positioned at the proximal end of the device 1800. In an example, the nozzle 1810 may be a Luer connection that enables devices, such as syringes, to be operably connected to the device 1800.

FIG. 20 illustrates a cross-sectional, side view of the medicinal fluid delivery device 1800 shown in FIGS. 18 and 19 in an advanced position in accordance with embodiments of the present disclosure. Referring to FIGS. 19 and 20, the mechanism 1802 includes a screw-type mechanism, generally designated 1900. As shown in FIG. 19, when a screw 1902 of the screw-type mechanism 1900 is tightened, the tube 1804 is retracted within the tube 1806. When the screw 1902 is loosened as shown in FIG. 20, the tube 1804 is extended out beyond the tube 1806.

FIGS. 21 and 22 illustrate a side, perspective view of the medicinal fluid delivery device 1800 shown in FIGS. 18, 19, and 20. In FIG. 21, the device 1800 is shown in the extended or advanced position. In FIG. 22, the device 1800 is shown in the retracted position.

FIGS. 23, 24, 25, and 26 illustrate a medicinal fluid delivery device 2300 having a rack-and-pinion mechanism 2302 for extending and retracting a delivery tube 2204 in accordance with embodiments of the present disclosure. The rack-and-pinion mechanism 2302 is contained in a housing 2304 that includes a connection component 2306 (e.g., a Luer connection). FIG. 23 illustrates a perspective view of the device 2300 in an extended position. FIG. 24 illustrates a side view of the device 2300 in a retracted position. FIG. 25 illustrates a cross-sectional side view of the device 2300 in a retracted position. FIG. 26 illustrates a cross-sectional side view of the device 2300 in an extended position.

Referring to FIGS. 25 and 26, the rack-and-pinion mechanism 2302 includes a geared piece 2500 that is in mechanical engagement with a geared dial 2502. The tube 2304 is connected to the geared piece 2500. The rack and pinion mechanism 2302 is encased in the housing 2304. The geared dial 2502 extends beyond the housing 2304 such that the user is able to turn a dial 2508 by use of a finger or by another technique. Turning of the dial 2508 effects the turning of the geared dial 2502.

As shown in FIG. 26, when the geared dial 2508 is rolled forward, the geared piece 2500 is retracted within the housing 2304, and the tube 2304 is retracted within tube 2310. This can be a position for inserting the device 2300 in the subject. Once inserted, the geared dial 2508 can be rolled backward thereby moving the geared piece 2500 forward within the housing 2304 and extending the tube 2304 from within the tube 2310.

Medicinal fluid delivery device according to embodiments of the present disclosure can provide the user control to precisely target locations in in the subject (e.g., the epidural and intrathecal space) to deliver substrates (e.g., cells and drugs) or other medicinal fluids. A device as disclosed herein can allow the user to finely control the advancement of the delivery tube, while allowing the user to manipulate the direction that the tube advances. The stability and solidarity of the device can minimize distal tip movement once positioned. The proximal portion of the device comprising the attachment component or connector (e.g., Luer lock) allows the user to connect any standard syringe/tube to the device for substrate delivery. For example, in an epidural injection, it can be important that the distal tip of the needle does not puncture the dura, so in some embodiments the delivery tube has an atraumatic tip. This may be from a coating that covers sharp edges or a material configuration such as reinforced tubing that is inherently less stiff than a nitinol tubing.

Devices in accordance with embodiments disclosed herein may be used in numerous methods for delivering a substrate to a subject. Generally, such methods comprise, consist of, or consist essentially of attaching the device a syringe or other container comprising the substrate to be delivered, retracting the second-co-axial delivery tube to be within the first co-axial introducer tube, inserting the device into the desired area of the subject, extending the second co-axial tube from within the first co-axial tube, optionally positioning the device to the desired spot within the subject, delivering the substrate to the subject, retracting the second co-axial delivery tube within the first co-axial introducer tube, and removing the device from the subject.

Suitable conditions for using the substrate device as provided herein include, but are not limited to, the following:

(a) Pain Management: Chronic pain such as low-back pain, arthritic pain, neuropathic pain, and cancer pain affects 30% Americans, and there is urgent need for safe and effective treatment of chronic pain. The device can deliver potential substrates including stem cells, drugs (targeted nerve blocks, growth factors) and direct pain pathway modulation to the Dorsal Root Ganglion (DRG). The DRG is an intraspinal structure that exists within the subdural or epidural space, as the dura extends out over the DRG. There is little CSF around the DRG so it can be advantageous to specifically target a location to achieve maximal cellular delivery. The devices disclosed herein can allow the user to deliver substrates with both an epidural and intrathecal approach, so that the user may target locations intrathecally along the DRG. To achieve maximum cell viability, the delivery tube provides flexibility and kink resistance as the substrates are administered. Also, for example, a device in accordance with the present disclosure can be used for epidural steroid injections, where the steroid is delivered transforaminally to where the nerve exits the spine via needle.

(b) Epidural Blood Patch (EBP): To treat Cerebral Spinal Fluid (CSF) leaks, doctors utilize CT Fluoroscopy to inject autologous blood and fibrin glue to create a seal of the dura to normalize the CSF hydrodynamics. Current methods of repair make it difficult to both access the ventral dural space and adequately spread the patch to stop the CSF leak. A recent study found although 96% of procedures were technically successful, only 47% resulted in an optimal epidurogram.[5] There is a need for a device to finely control and advance the distal tip of a delivery tube to navigate the delicate anatomy as to not cause another dural leak. Using a standard spinal needle with a traditional lateral approach, EBPs can only be delivered to the ipsilateral aspect of ventral space. However, with the proposed substrate delivery device, the user can advance the needle around and across the epidural space to access the difficult to reach central and contralateral surfaces of the ventral dura.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A medicinal fluid delivery device comprising:
   a tube including a first opening and a second opening, the tube defining an interior space that extends between the first opening and the second opening, and the interior space having an interior wall;
   a needle being at least partially positioned within the interior space of the tube, wherein the needle comprises a proximal end and a distal end that substantially align in a first direction, wherein a portion of the distal end is biased to extend in a second direction that is different than the first direction; and
   a mechanism comprising a needle engagement portion attached to the proximal end of the needle and configured to position the distal end between a first position and a second position, wherein the needle engagement portion defines ridges that form a channel therebetween, wherein the channel mechanically engages the proximal end of the needle, wherein in the first position the portion of the distal end is constrained by the interior wall such that it does not extend in the second direction, and wherein in the second position the portion of the distal end is not constrained by the interior wall such that it extends in the second direction.

2. The medicinal fluid delivery device of claim 1, wherein the portion of the distal end is made of shape-memory material.

3. The medicinal fluid delivery device of claim 2, wherein the shape-memory material is made of nickel-titanium or copper-aluminum-nickel.

4. The medicinal fluid delivery device of claim 1, wherein the portion of the distal end has a curved shape.

5. The medicinal fluid delivery device of claim 1, wherein the first and second directions have an angle measurement of between about 15 degrees and about 75 degrees.

6. A medicinal fluid delivery device comprising:
   a tube including a first opening and a second opening, the tube defining an interior space that extends between the first opening and the second opening, and the interior space having an interior wall;
   a needle being at least partially positioned within the interior space of the tube, wherein the needle comprises a proximal end and a distal end that substantially align in a first direction, wherein a portion of the distal end is biased to extend in a second direction that is different than the first direction wherein the portion of the distal end is made of shape-memory material, wherein the portion of the distal end is made of shape-memory material, and wherein the distal end of the needle is positionable between a first position and a second position, wherein in the first position the distal end is within the interior space and the portion of the distal end is constrained by the interior wall such that is does not extend in the second direction, and wherein in the second position the distal end is outside the interior space such that the portion of the distal end is not constrained by the interior wall such that it extends in the second direction; and a mechanism comprising a needle engagement portion attached to the proximal end of the needle and configured to position the distal end between a first position and a second position, wherein the needle engagement portion defines ridges that form a channel therebetween, wherein the channel mechanically engages the proximal end of the needle.

7. The medicinal fluid delivery device of claim 6, wherein the shape-memory material is made of nickel-titanium or copper-aluminum-nickel.

8. The medicinal fluid delivery device of claim 6, wherein the portion of the distal end has a curved shape.

9. The medicinal fluid delivery device of claim 6, wherein the first and second directions have an angle measurement of between about 15 degrees and about 75 degrees.

10. A method of medicinal fluid delivery, the method comprising:
   providing a medicinal fluid delivery device comprising:
      a tube including a first opening and a second opening, the tube defining an interior space that extends between the first opening and the second opening, and the interior space having an interior wall;
      a needle being at least partially positioned within the interior space of the tube, wherein the needle comprises a proximal end and a distal end that substantially align in a first direction, wherein a portion of the distal end is biased to extend in a second direction that is different than the first direction;
      a mechanism comprising a needle engagement portion attached to the proximal end of the needle and configured to position the distal end between a first position and a second position, wherein the needle engagement portion defines ridges that form a channel therebetween, wherein the channel mechanically engages the proximal end of the needle; and
   moving needle engagement portion to thereby move the needle between a first position and a second position, wherein in the first position the distal end is within the interior space and the portion of the distal end is constrained by the interior wall such that is does not extend in the second direction, and wherein in the second position the distal end is outside the interior space such that the portion of the distal end is not constrained by the interior wall such that it extends in the second direction.

11. The method of claim 10, further comprising during position at the first position, using the needle to deliver medicinal fluid to a target area of a subject.

12. The method of claim 10, wherein moving the needle engagement portion comprises using the needle engagement portion to move the needle between the first position and the second position.

13. The method of claim 10, wherein the portion of the distal end is made of shape-memory material.

14. The method of claim 10, wherein the shape-memory material is made of nickel-titanium or copper-aluminum-nickel.

15. The method of claim 10, wherein the portion of the distal end has a curved shape.

16. The method of claim 10, wherein the first and second directions have an angle measurement of between about 15 degrees and about 75 degrees.

* * * * *